Figure 4:
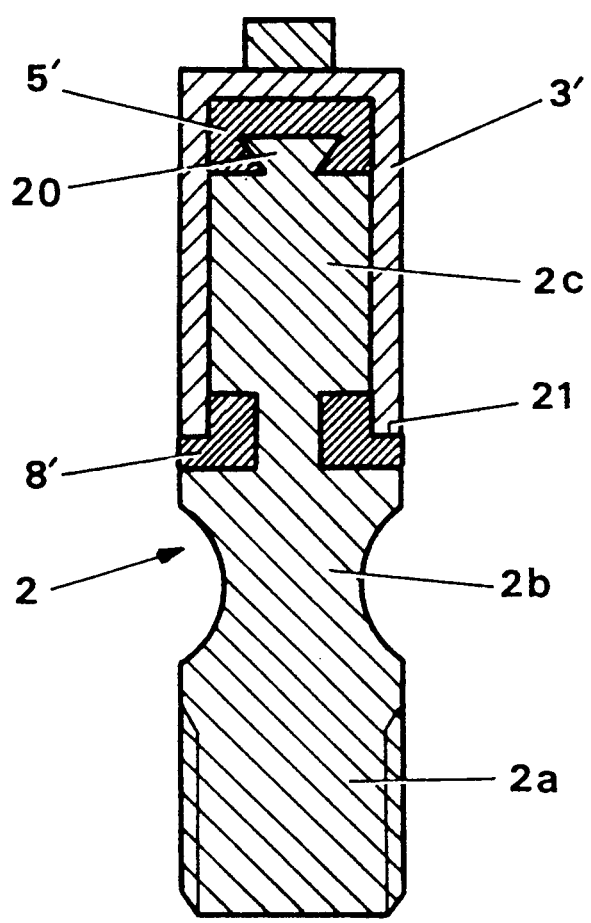

United States Patent [19]

Scatena

[11] Patent Number: 5,033,962
[45] Date of Patent: Jul. 23, 1991

[54] STUMP TO BE FIXED TO THE ENDOSTAL PART OF A DENTAL IMPLANT

[76] Inventor: Aldo Scatena, viale G. Pucci 425 bis, I-5100 Lucca, Italy

[21] Appl. No.: 469,582

[22] PCT Filed: Sep. 28, 1988

[86] PCT No.: PCT/EP88/00878
§ 371 Date: May 4, 1990
§ 102(e) Date: May 4, 1990

[87] PCT Pub. No.: WO89/03200
PCT Pub. Date: Apr. 20, 1989

[30] Foreign Application Priority Data

Oct. 8, 1987 [IT] Italy ................... 48468A/87

[51] Int. Cl.[5] ............................. A61C 13/28
[52] U.S. Cl. ....................... 433/169; 433/173
[58] Field of Search ............. 433/169, 172, 170, 173

[56] References Cited

U.S. PATENT DOCUMENTS

| | | | |
|---|---|---|---|
| 2,854,746 | 10/1958 | Lester et al. | 433/169 |
| 4,746,293 | 5/1988 | Lundgren | 433/169 |
| 4,756,689 | 7/1988 | Lundgren | 433/169 |
| 4,938,693 | 7/1990 | Bulakiev | 433/169 |

FOREIGN PATENT DOCUMENTS 494239  5/1954  Italy ..................... 433/169

Primary Examiner—Cary E. Stone
Attorney, Agent, or Firm—Woodward, Emhardt, Naughton, Moriarty & McNett

[57] ABSTRACT

A stump comprising a central core having a head part and a lower part provided with means for fixing the stump to an implant, and a cap for covering at least a part of the head part, at least one elastic element being arranged at the cap/central core interface. The assembly is arranged so as to permit relative movement between the cap and the central core. Restraining elements are provided to limit the relative vertical movement between the cap and the central core.

9 Claims, 2 Drawing Sheets

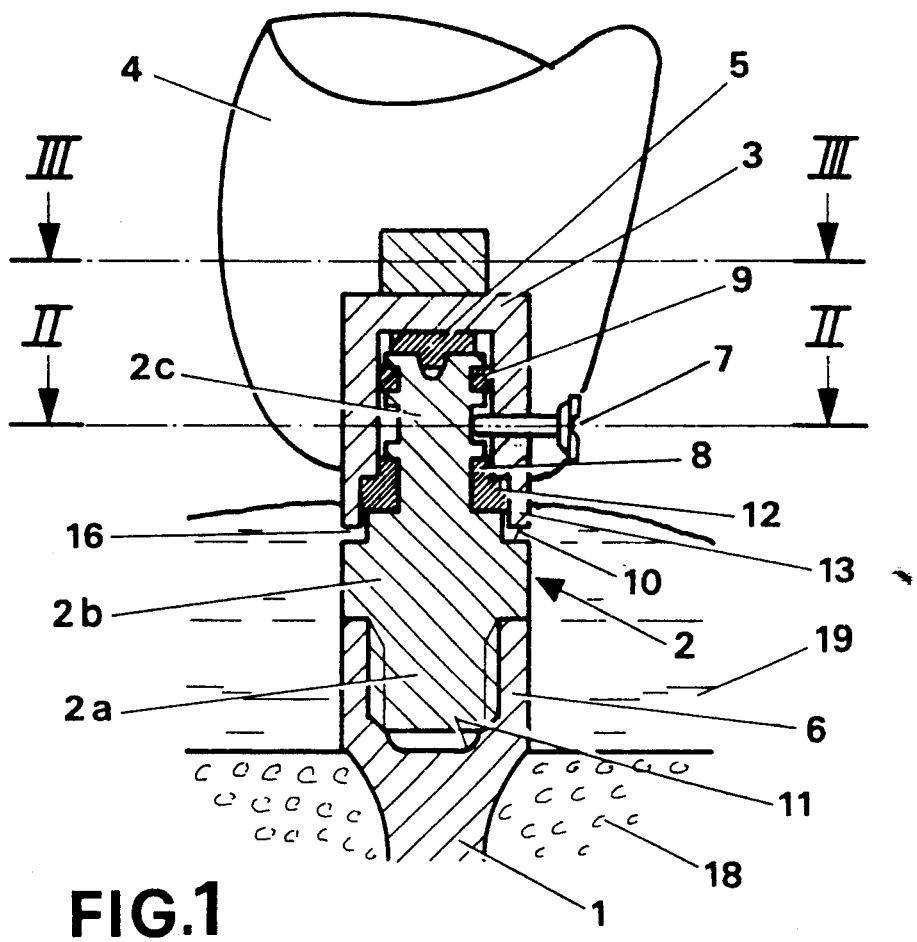
FIG.1
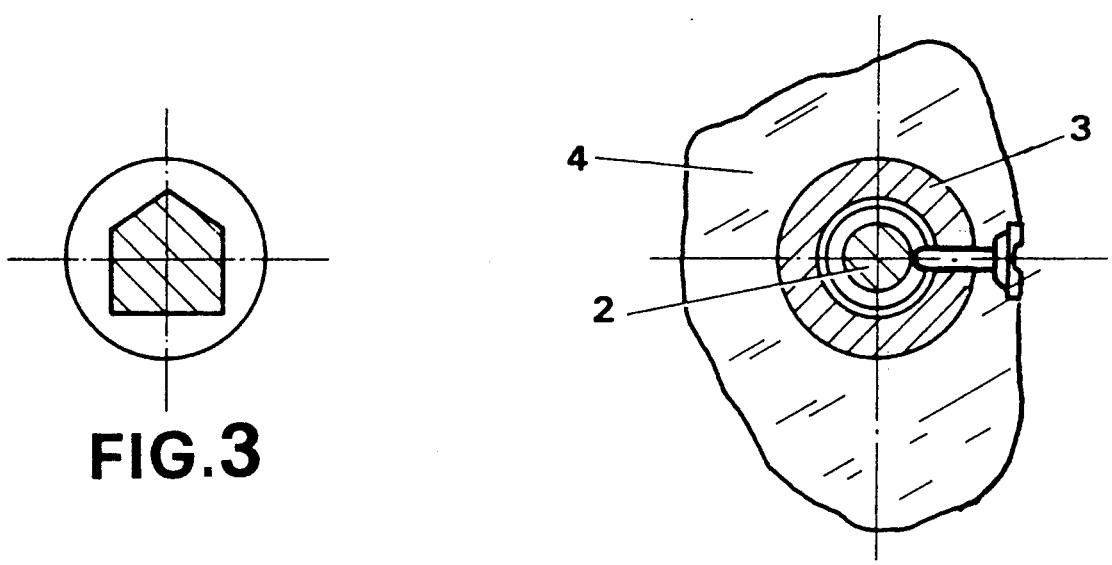
FIG.3
FIG.2

STUMP TO BE FIXED TO THE ENDOSTAL PART OF A DENTAL IMPLANT

The present invention is concerned with a stump to be fixed to the endostal part of a dental implant, which is of the type described in the preamble of claim 1.

Dental implants of several types are known, such as for example implants with blades, implants with screws, etc. These implants are generally comprised of a so-called endostal part, which is designed to be implanted into the jawbone and a head part designed to protrude above the gum and to support a tooth or a prosthesis, with the two parts forming an integral body. These implants have the disadvantage of forming hard points with respect to the neighboring teeth, which, when they are healthy, have a resiliency of about 0.2 millimeters.

An implant capable of remedying partly the above drawbacks is described in French Patent 1'584'711. This implant is comprised of a body fixed on a rider resting on the maxillary, said body being provided with an inner threading for receiving the threaded end of a cylindrical piece covered with a cap integral with the prosthesis, said cap being capable of sliding axially and resiliently on the cylindrical piece, an elastic element being arranged at the interface cap/cylindrical piece at the upper end of said cylindrical piece. Such an implant functions well only when the force applied on the prosthesis acts primarily vertically, i.e. in the direction of the implant axis. In practice however, this ideal situation is rather exceptional and, generally, the horizontal component of the force exerted on the prosthesis is important. Accordingly, the implant described in the French Patent 1'584'711 does not make it possible to re-create the physiological conditions of a healthy tooth.

The purpose of the invention is to provide a stump to be fixed to the endostal part of a dental implant, which makes it possible to re-create the physiological conditions corresponding to those of a healthy tooth, in order to remedy the drawbacks of known implants.

Accordingly, the object of the invention is a stump designed to be fixed to the endostal part of a dental implant, comprising a central core having a head part and a lower part provided with means for fixing the stump to the implant, and a cap for covering at least a part of said head part, a first elastic element being arranged at the interface cap/central core at the upper end of the head part, a second elastic element being arranged at the interface cap/central core in a first groove provided along the periphery of the head part of the central core, the assembly being arranged so as to permit relative movement between the cap and the central core, laterally arranged restraining elements being provided to limit the relative vertical movement between the cap and the central core.

According to one embodiment of the invention, the first groove is provided along the periphery of the head part of the central core, at the level of the lower end of the cap, the cap being supported by said second elastic element.

According to one version of the invention, at least a third elastic element is arranged at the interface cap/central core, inside a second groove provided along the periphery of the head part of said central core, between the first groove and the upper end of the head part of the central core, the stump being capable of comprising at least a third groove provided along the periphery of the stump, the restraining means comprising a locking means, one end of which, having outer dimensions lesser than the width of said third groove, is engaged inside the third groove.

The third groove can be located between the first and the second groove.

The second elastic element can be arranged so as to provide a surface for supporting vertically the cap and a surface for supporting laterally said cap.

The lower end of the cap can comprise an inner ledge intended for supporting vertically the cap by the second elastic element and a peripherally protruding part which is positioned opposite an upper outer ledge of the lower part of the central core, and arranged to provide an abutment for the relative movements between the cap and the central core.

According to another version of the invention, the outer dimensions of the first elastic element are appreciably greater than the outer dimensions of the head part of the central core, the second elastic element comprising an upper part with outer dimensions appreciably greater than the outer dimensions of the head part of the central core and a lower part with outer dimensions greater than those of the upper part thereof, so as to provide a horizontal ledge to support vertically the cap, the securing of the cap to the central core being ensured by the friction of the inner wall of the cap against the vertical outer surfaces of the elastic elements, the first elastic element being secured against the upper end of the head part of the central core by a restraining means integral with the central core.

Whatever the embodiment may be, the central core and the cap can have a generally cylindrical shape.

The invention will be better understood from the following description, given by way of example, with reference to the drawings, wherein:

FIG. 1 is a vertical cross-section of a first example of a stump according to the invention, FIG. 2 is a horizontal cross-section taken along line II—II of FIG. 1, FIG. 3 is a horizontal cross-section taken along line III—III of FIG. 1, and FIG. 4 is a vertical cross-section of a second example of a stump according to the invention.

The stump shown in FIGS. 1 to 3 is fixed to the endostal part 1 of a dental implant anchored to the bone 18 of the lower jaw. The upper end 6 of the endostal part comprises a housing 11 provided with an inside threading into which is screwed the lower part of the central core of a stump 2. The stump, preferably of a cylindrical shape, comprises a central core 2 which includes a lower part 2a provided with an outer threading designed to be screwed inside the housing 11 of the endostal part of the implant, a base part 2b and an upper part 2c. The upper part 2c of the central core comprises three horizontal grooves provided along the outer periphery thereof, namely a lower groove, a medial groove and an upper groove. A cap 3 covers the upper part of the central core. The inner diameter of the cap is selected to leave a small clearance between the cap and the outer diameter of the upper part of the central core, so that the cap can be slidably fitted on the upper part of said central core and so that it may move vertically and laterally with respect to the central core. The base part 2b of the central core has an outer diameter equal to the outer diameter of the cap and comprises an upper part with a reduced outer diameter, to form a horizontal peripheral ledge 10. The inner diameter of the lower end 13 of the cap is greater than the inner diameter of the cap body, so as to provide a horizontal peripheral ledge 12. A first elastic element 8, arranged inside the lower groove of the central core comprises an upper part, the diametral thickness of which is appreciably greater than the depth of the groove, and a lower part, the outer diameter of which is greater than the outer diameter of the upper part thereof, so as to form an outward shoulder to support the cap laterally and vertically at the inner edge thereof forming the ledge 12. A second elastic element 9 is arranged inside the upper groove of the central core, the thickness of said elastic element being appreciably greater than the depth of said upper groove. A third elastic element 5 or cushion is arranged beneath the cap, at the upper end of the central core. In the unstressed condition, a gap 16 appears between the lower end 13 of the cap and the peripheral ledge 10 of the central core. This gap leaves the cap free to move vertically and horizontally with respect to the central core, when the first and the third elastic elements 8 and 5 are compressed by the effect of a load acting on the tooth 4 fixed to the cap 3. The locking of the cap onto the central core is achieved by means of a screw 7, which is screwed inside a bore extending through the tooth and the wall of the cap. This screw 7 comprises an end part which protrudes inside the cap to engage inside the medial groove. The outer diameter of the end part of the screw is smaller than the height of the medial groove, so as to allow a relative movement between the cap and the central core when the elastic elements 8 and 5 are compressed under the effect of the load. The thickness of the lower part of the first elastic element 8, as well as the thickness of the elastic element 5, can be selected to amount to 0.5 millimeters. The assembly thus constructed re-creates perfectly the physiological conditions of a tooth, since it allows the cap and hence the tooth, to make lateral movements, as a result of the presence of the elastic elements 8 and 9, in addition to the vertical movements authorized by the elastic elements 8 and 5.

In order to limit the relative vertical movement between the cap and the central core, the height of the lower end part 13 of the cap is selected so as to have a gap 16 between said end part and the peripheral ledge 10 of the central core in the order of 0.2 millimeters. This limitation is made, in case the quality of the elastic elements should deteriorate.

In order to increase the flexibility of the assembly, the dimension of the outer diameter of the base part can be reduced in the medial part thereof.

The second example of a stump shown in FIG. 4 comprises a central core 2 having a generally cylindrical outer shape and also having a lower part 2a provided with an outer threading, which is designed for being screwed inside the corresponding housing of the endostal part of a dental implant. The upper part 2c of the central core comprises at the upper end thereof a dovetail-shaped protrusion 20, onto which is fixed and secured a first elastic element 5', the outer diameter of which is appreciably greater than the outer diameter of the upper part 2c of the central core. A second elastic element 8' is fitted inside a peripheral groove provided at the base of the upper part 2c of the central core. This second elastic element comprises an upper part, the outer diameter of which is appreciably greater than the outer diameter of the upper part 2c of the central core, and a lower part having an outer diameter greater than that of the upper part, so as to form a ledge 21 to support a cap 3', also of a cylindrical shape and having an inner diameter which leaves a small clearance between said cap and the outer diameter of the upper part 2c of the central core. The presence of the two elastic elements permits a vertical movement of the cap with respect to the central core, due to the resiliency of the elastic elements, the cap being however kept in position on the central core by the friction exerted by said elastic elements against the inner wall thereof. In order to increase the lateral flexibility of the assembly, the base part 2b of the central core, the upper part of which has a diameter equal to that of the outer diameter of the cap, has a reduced diameter in the medial part thereof.

The elastic elements can be made, for example, of synthetic resin, of any material having rubber components, of food-grade rubber, or of any other appropriate material. Quite obviously, other types of elastic elements can be used, depending on circumstances, such as for example springs.

The above described device can be applied to any known implants, whether they be made of titanium, of ceramic, of aluminium bioxide or of any other material, and whatever may be the shape of the implant.

I claim:

1. A stump designed to be fixed on a dental implant, comprising a central core (2) having a head part (2c) and a lower part (2a, 2b) provided with means for fixing the stump to the implant, and a cap (3) for covering at least a part of said head part, a first elastic element (5) being arranged at the cap/central core interface at the upper end of the head part, the assembly being arranged so as to permit relative movement between the cap and the central core, restraining elements arranged laterally being provided to limit the relative vertical movement between the cap and the central core, characterized in that a second element (8) is arranged at the cap/central core interface inside a first groove provided along the periphery of the head part of the central core, at the level of the lower end of the cap, said second elastic element comprising elements which make it possible to support vertically and laterally the cap on said second elastic element.

2. A stump according to claim 1, characterized in that at least a third elastic element (9) is arranged at the interface cap/central core inside a second groove provided along the periphery of the head part of said central core, between the first groove and the upper end of the head part of the central core.

3. A stump according to claim 2, characterized in that a third groove is provided along the periphery of the stump, and in that the restraining elements comprise a locking element (7), one end of which, having outer dimensions lesser than the width of said third groove, is engaged inside the third groove.

4. A stump according to claim 3, characterized in that the third groove is located between the first and the second groove.

5. A stump according to claim 2, characterized in that the second elastic element (8) is arranged so as to provide a surface for supporting vertically the cap and a surface for supporting laterally said cap.

6. A stump according to claim 2, characterized in that the lower end of the cap comprises an inner ledge designed for supporting vertically the cap on the second elastic element and a protruding peripheral part which is positioned opposite an outer upper ledge of the lower part of the central core, and arranged so as to provide an abutment for the relative movements between the cap and the central core.

7. A stump according to claim 1, characterized in that the outer dimensions of the first elastic element are appreciably greater than the outer dimensions of the head part of the central core, the second elastic element comprising an upper part with outer dimensions appreciably greater than the outer dimensions of the head part of the central core and a lower part with outer dimensions greater than those of the upper part thereof, so as to provide a horizontal ledge (21) for supporting vertically the cap, the securing of the cap onto the central core being achieved through the friction of the inner wall of the cap against the vertical outer surfaces of the elastic elements, the first elastic element being secured to the upper end of the head part of the central core by a restraining element (20) integral with the central.

8. A stump according to claim 1, characterized in that the restraining elements include a screw (7), which is screwed through a tooth that is supported by the implant and the cap wall, said screw comprising an end part which protrudes inside the cap and which is engaged inside a housing provided in the head part of the central core, the dimensions of said housing being greater than the diameter of the end of the screw, to permit relative movement between the cap and the central core, when the elastic elements are compressed.

9. A stump according to claim 1, characterized in that the central core and the cap are of a generally cylindrical shape.

* * * * *

UNITED STATES PATENT AND TRADEMARK OFFICE
CERTIFICATE OF CORRECTION

PATENT NO. : 5,033,962
DATED : July 23, 1991
INVENTOR(S) : Aldo Scatena

It is certified that error appears in the above-identified patent and that said Letters Patent is hereby corrected as shown below:

On the title page:
In item [76] Inventor, please delete "I-5100" and insert in lieu thereof --I-55100--.

In the name of the Attorney, Agent, or Firm, please delete "Woodward" and insert in lieu thereof --Woodard--.

In column 6, line 2, after the word "central" and before the period, insert the word --core--.

Signed and Sealed this

Fifth Day of May, 1992

Attest:

DOUGLAS B. COMER

*Attesting Officer*      *Acting Commissioner of Patents and Trademarks*